United States Patent
Podrebarac et al.

(10) Patent No.: US 10,961,169 B2
(45) Date of Patent: Mar. 30, 2021

(54) SYSTEMS AND PROCESSES FOR MAINTAINING ETHYLBENZENE DEHYDRATION CATALYST ACTIVITY

(71) Applicant: LUMMUS TECHNOLOGY LLC, Bloomfield, NJ (US)

(72) Inventors: Gary George Podrebarac, Friendswood, TX (US); Kevin John Schwint, Long Valley, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/388,564

(22) Filed: Apr. 18, 2019

(65) Prior Publication Data
US 2020/0331825 A1    Oct. 22, 2020

(51) Int. Cl.
C07C 5/367    (2006.01)
C07C 5/32     (2006.01)
(Continued)

(52) U.S. Cl.
CPC .............. *C07C 5/367* (2013.01); *C07C 5/324* (2013.01); *B01J 4/002* (2013.01); *B01J 19/26* (2013.01); *C07C 15/46* (2013.01); *C07C 2523/04* (2013.01)

(58) Field of Classification Search
None
See application file for complete search history.

(56) References Cited

U.S. PATENT DOCUMENTS 4,590,324 A * 5/1986 Satek .................... C07C 5/3335
                                                        585/444
5,358,698 A  10/1994 Butler et al.
(Continued)

FOREIGN PATENT DOCUMENTS

CN    101992129 A    3/2011

OTHER PUBLICATIONS

Gaverick, Linda "Chapter 4: Corrosion in the Chemical Processing Industry" Corrosion in the Petrochemical Industry (1994). pp. 163-174 (Year: 1994).*
(Continued)

*Primary Examiner* — Philip Y Louie
*Assistant Examiner* — Alyssa L Cepluch
(74) *Attorney, Agent, or Firm* — Osha Bergman Watanabe & Burton LLP

(57) ABSTRACT

Processes and systems for dehydrogenating ethylbenzene may include mixing a steam stream and an ethylbenzene stream to form a feed mixture. The ethylbenzene/steam feed mixture may then be fed to a dehydrogenation reactor containing an alkali metal promoted catalyst. A liquid, selected from an alkali metal liquid, an alkali metal compound liquid, or a liquid solution comprising an alkali metal, may be injected into a feed stream, such as the steam stream, the ethylbenzene stream, or the ethylbenzene/steam feed mixture. Following injection, the liquid vaporizes and disperses into the feed stream upstream of the dehydrogenation reactor. The liquid may be maintained as a liquid from a point upstream of injection to an injection nozzle. The liquid is dispersed through the injection nozzle, in liquid form, to form droplets of liquid dispersed in the feed stream, which evaporate and/or dissolve into the vaporous feed stream.

9 Claims, 3 Drawing Sheets

(51) Int. Cl.
  *C07C 15/46* (2006.01)
  *B01J 4/00* (2006.01)
  *B01J 19/26* (2006.01)

(56) References Cited

U.S. PATENT DOCUMENTS

| | | |
|---|---|---|
| 5,739,071 A | 4/1998 | Chen et al. |
| 6,936,743 B2 | 8/2005 | Butler |
| 8,648,007 B2 | 2/2014 | Pelati et al. |
| 2006/0183953 A1 | 8/2006 | Ledoux et al. |
| 2006/0224029 A1 | 10/2006 | Butler |
| 2009/0118557 A1 | 5/2009 | Merrill et al. |
| 2009/0312589 A1 | 12/2009 | Schwint et al. |

OTHER PUBLICATIONS

International Search Report issued in corresponding International Application No. PCT/US2019/028159, dated Jan. 15, 2020 (3 pages).
Written Opinion issued in corresponding International Application No. PCT/US2019/028159, dated Jan. 15, 2020 (6 pages).

\* cited by examiner

SYSTEMS AND PROCESSES FOR MAINTAINING ETHYLBENZENE DEHYDRATION CATALYST ACTIVITY

FIELD OF THE DISCLOSURE

Embodiments disclosed herein relate generally to the dehydrogenation of alkyl aromatics to form alkenyl aromatics, such as the dehydrogenation of ethylbenzene to form styrene. More specifically, embodiments herein relate to the processes and systems for maintaining catalyst activity within the dehydrogenation reactor.

BACKGROUND

During the dehydrogenation of ethylbenzene to make styrene, the iron-oxide catalyst deactivates. One of the main reasons for catalyst deactivation is the migration of the potassium promoter in the catalyst. Injection of a small quantity of potassium solution with the mixed ethylbenzene/water (steam) feed has been proposed to discourage potassium migration and maintain the catalyst in an active form for a longer period of time. Steam, methane and inert gas have been proposed as carriers to transport the solution into the EB feed. However, heating and vaporization of a solution of potassium hydroxide or a potassium salt can cause the salt to precipitate and plug the transfer pipe.

U.S. Pat. No. 6,936,743 teaches that the life of a potassium or chromium stabilized dehydrogenation catalyst can be extended by injecting 0.1 to 10 ppm of a "catalyst life extender." A life extender noted is potassium acetate.

U.S. Pat. No. 5,739,071 teaches that the life of an iron-based/alkali metal stabilized catalyst can be extended by continuous injection of alkali metal or alkali metal compound, such as injection of about 0.01 to 100 ppm of the alkali metal or the alkali metal compound. Compounds noted include potassium hydroxide, potassium carbonate, and potassium oxide. Metals are also noted, including potassium or sodium metal. The '071 patent teaches that inert nitrogen can be used to carry the vaporized alkali metal or alkali metal compound into the reactor feed stream.

U.S. Pat. No. 8,648,007 teaches that the injection of potassium salts must be done carefully, or the potassium salt can deposit in the injection device. In examples, the temperature of the vaporization device needed to be between 200° C. and 480° C. for the injection of a 10% potassium acetate solution.

US20060224029 discloses that Cs compounds can be used to extend the life of Fe-based dehydrogenation catalysts.

Heating and vaporization of a solution of potassium hydroxide or a potassium salt can cause the salt to precipitate and plug the transfer pipe. Work is presented in the patents noted above, such as the '007 patent, as a solution to this problem. However, it is hard to volatilize a potassium salt because the melting points are quite high. For example, KOH melts at 360° C., K2CO3 melts at 891° C., K-acetate melts at 292° C., and K2SO4 melts at 1069° C. As such, systems in the '007 patent may still be prone to plugging if there is some sort of operational upset or a compound other than potassium acetate is used.

SUMMARY OF THE DISCLOSURE

Processes and systems have now been developed to inject potassium, either as a pure metal or a dissolved hydroxide or a dissolved salt, to avoid plugging in the injection system. In contrast to existing systems, embodiments herein may inject molten potassium metal or a solution of potassium salt or potassium hydroxide directly into the EB feed, the main steam line, or the main EB/steam feed that is going into the reactor. The injection nozzle may be designed to limit the heat transfer into the potassium or potassium solution, so that the potassium or potassium solution does not boil until it passes through the nozzle and into the hot stream of steam, EB, or EB/steam. Following injection, the potassium or potassium compound may evaporate in the process pipe before they reach the catalyst bed and thoroughly mix with the feed stream so that the potassium is well dispersed throughout the catalyst bed. While prior practice focused on vaporizing the material prior to injecting it into the reactor feed, embodiments herein use a different approach, and purposely do not vaporize the potassium, potassium compound, or potassium solution prior to the injection.

In one aspect, embodiments disclosed herein relate to processes for dehydrogenating ethylbenzene. The processes may include mixing a steam stream and an ethylbenzene stream to form an ethylbenzene/steam feed mixture. The ethylbenzene/steam feed mixture may then be fed to a dehydrogenation reactor containing an alkali metal promoted catalyst to convert a portion of the ethylbenzene to styrene. A liquid, selected from an alkali metal liquid, an alkali metal compound liquid, or a liquid solution comprising an alkali metal, may be injected into a feed stream comprising at least one of the steam stream, the ethylbenzene stream, or the ethylbenzene/steam feed mixture. Following injection, the liquid vaporizes and disperses into the feed stream upstream of the dehydrogenation reactor. The liquid (the alkali metal, the alkali metal compound liquid, or the liquid solution comprising an alkali metal) may be maintained in a liquid state from a point upstream of injection to an injection nozzle. The liquid is dispersed through the injection nozzle, in liquid form, to form droplets of liquid dispersed in the feed stream, after which point the liquid evaporates and/or dissolves into the vaporous feed stream.

In another aspect, embodiments disclosed herein relate to systems for maintaining catalyst activity in an ethylbenzene dehydrogenation reactor. The systems may include a liquid alkali feed stream, where the feed stream is heated or insulated, as needed, to maintain in a liquid state a liquid alkali feed selected from at least one of an alkali metal, an alkali metal compound liquid, and a liquid solution comprising an alkali metal. The system may also include an injection nozzle for injecting the liquid alkali feed, as a liquid, into a process feed stream selected from a steam stream, an ethylbenzene feed stream, and an ethylbenzene/steam feed stream to form an alkali-containing feed. The system also includes a dehydrogenation reactor containing an alkali metal promoted catalyst and having an inlet for receiving the alkali-containing feed or a mixture comprising the alkali-containing feed.

To maintain the liquid feed in the liquid state, the alkali feed stream may be steam traced, insulated, or coolant traced upstream of the injection nozzle. The steam tracing, insulation, etc., may be continued up to the injection nozzle, or as close as may be practicable.

In some embodiments, the system may further include a water feed stream fluidly connected to the injection nozzle. A control system may be provided, in some embodiments, to alternate feed of the liquid alkali feed and the water feed stream to the injection nozzle.

In another aspect, embodiments disclosed herein relate to processes for maintaining catalytic activity in a reactor. The processes may include injecting a liquid comprising a catalyst rejuvenating compound into a vaporous feed stream comprising an inert and/or a reactant upstream of an inlet of a reactor. The liquid may be vaporized and dispersed into the vaporous feed stream within a flow pipe upstream of the reactor to form a vaporous mixture comprising the catalyst rejuvenating compound and at least one of an inert or a reactant. A catalyst contained within the reactor may be contacted with the vaporous catalyst rejuvenating compound to enhance an activity of the catalysts within the reactor, while the catalyst in the reactor is concurrently performing its intended reaction.

Other aspects and advantages will be apparent from the following description and the appended claims.

DETAILED DESCRIPTION

Embodiments disclosed herein relate generally to the dehydrogenation of alkyl aromatics, such as alkylbenzenes, to form alkenyl aromatics, such as for the dehydrogenation of ethylbenzene to make styrene. More specifically, embodiments herein relate to the processes and systems for maintaining catalyst activity within the dehydrogenation reactor. Even more specifically, embodiments herein relate to the injection of catalyst rejuvenating compounds into a reaction system. For example, embodiments herein may be directed toward the injection of potassium or potassium compounds to maintain catalyst activity within the dehydrogenation reactor.

Embodiments herein are described below in relation to dehydrogenation of ethylbenzene to form styrene. However, one skilled in the art can readily appreciate that the processes disclosed herein may be applicable to processes for the dehydrogenation of other alkylaromatic hydrocarbons to form alkenyl aromatic hydrocarbons, such as for the dehydrogenation of cumene to form alpha methyl styrene, ethyltoluene to form vinyl toluene, and many numerous other alkenyl aromatic compounds. Processes for the dehydrogenation of butane to form butadiene, as well as other conversion processes, such as dealkylation of alkylaromatics, synthesis of ammonia, synthesis of maleic anhydride, and other conversion processes may also benefit from embodiments herein.

Figure 1:
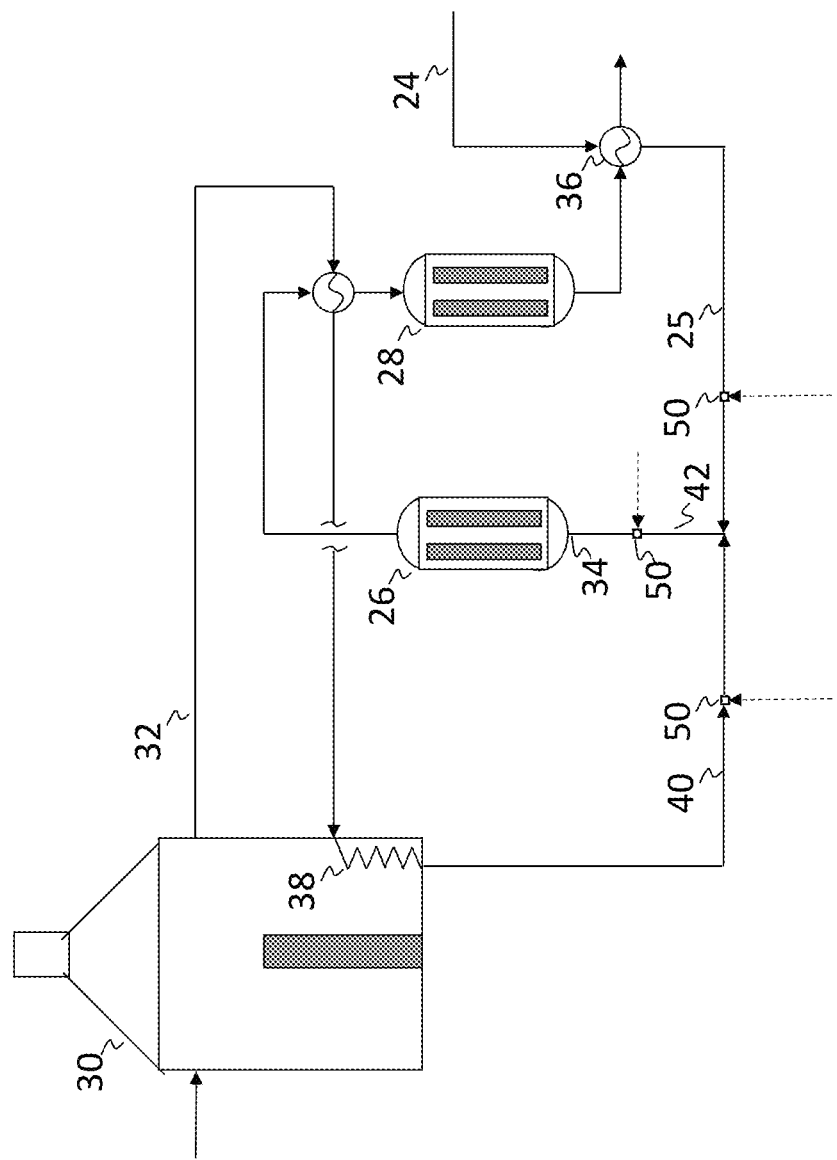
FIG. 1 is a simplified process flow diagram of a system for the dehydrogenation of ethylbenzene to form styrene according to embodiments herein.

Referring now to FIG. 1, a simplified flow diagram of a typical configuration for the dehydrogenation reaction area of a styrene plant is illustrated. Styrene monomer is manufactured by dehydrogenating the ethylbenzene (EB) feed, which is an endothermic reaction. A vaporized azeotropic mixture of ethylbenzene and water is fed via flow line 24 to the reaction zone, which may include two to four dehydrogenation reactors 26, 28. The effluent from each reactor 26 may be reheated using steam before entering the next reactor 26 or final reactor 28. The steam used for reheating the reactor effluents is commonly referred to as Main Steam (MS), which is provided from a steam superheater 30 via flow line 32 and coil 38 and eventually enters at the inlet 34 of the first reactor 26 along with the vaporized EB/water mixture, which may also be preheated against the effluent from final reactor 28 in exchanger 36. FIG. 1 is an exemplary dehydrogenation system, and other processes and systems for dehydrogenating ethylbenzene may also benefit from embodiments herein.

As noted above, the catalyst contained in reactors 26, 28 may lose activity due to migration of catalytic or co-catalytic components. It is desirable to inject compounds to help maintain or retain activity of the catalyst, thereby extending the catalyst life and the overall run time of the reaction system before necessary shutdown and catalyst replacement. For example, a potassium stabilized dehydrogenation catalyst may benefit from the introduction of potassium or a potassium compound into the reactor. Embodiments herein may provide the potassium in a useful form, with minimal or no buildup of potassium or potassium salts in the injection system or the associated piping.

Processes and systems disclosed herein may thus be used to inject molten potassium metal or a solution of potassium salt or potassium hydroxide directly into a vaporized reactor feed stream via one or more injection systems 50. For example, the liquid metal or solution may be introduced to ethylbenzene (EB) feed 24/25, the main steam line 40, or the main EB/steam feed 42 that is going into the reactor 26 via one or more injection systems 50. In some embodiments, for example, molten, liquid potassium may be injected into the EB/steam stream.

Potassium metal melts at about 63.5° C. A steam traced vessel may be used to store the potassium metal, and steam traced or insulated piping may maintain the metal in a liquid form and allow it to flow into the process unit. The liquid potassium may be metered directly into the pipe containing the EB/steam feed to the dehydrogenation reactor, such as stream 42 as illustrated in FIG. 1, for example. Potassium boils at approximately 759° C. Generally, the feed to the dehydrogenation reactor is at a temperature in the range of 500° C. to about 650° C. The process temperature of the EB/steam is hot enough to keep the potassium melted, but not hot enough to boil the potassium.

The potassium metal may be sprayed or atomized with nitrogen, or another appropriate inert gas, through a nozzle into the EB/steam feed mixture, for example. As the potassium metal will not be boiled or vaporized in the piping leading to the nozzle, it will not leave behind any fouling deposits that can plug the line. The expected feed rate of potassium into the system may be, for example, 50 to 1000 g/h, depending upon the size of the reactor and catalyst content, and thus the feed rate may be controlled with commonly available components.

In other embodiments, a solution of a potassium salt or potassium hydroxide may be injected into the EB/steam stream upstream of the reactor 26. Potassium salts dissolved in water may start to boil or could mostly vaporize in the pipe leading to the injection nozzle, resulting in deposits of precipitated potassium salt or potassium hydroxide in the pipe, plugging the system. The boiling point of a 50 wt % solution of KOH in water is about 145° C., which is much cooler than the 500° C. to 650° C. temperature of the feed to the reactor. However, according to embodiments herein, a potassium solution is injected into the reactor feed via an insulated pipe, maintaining the potassium solution at a low enough temperature such that the solution will not boil and the nozzle will not foul.

Figure 2:
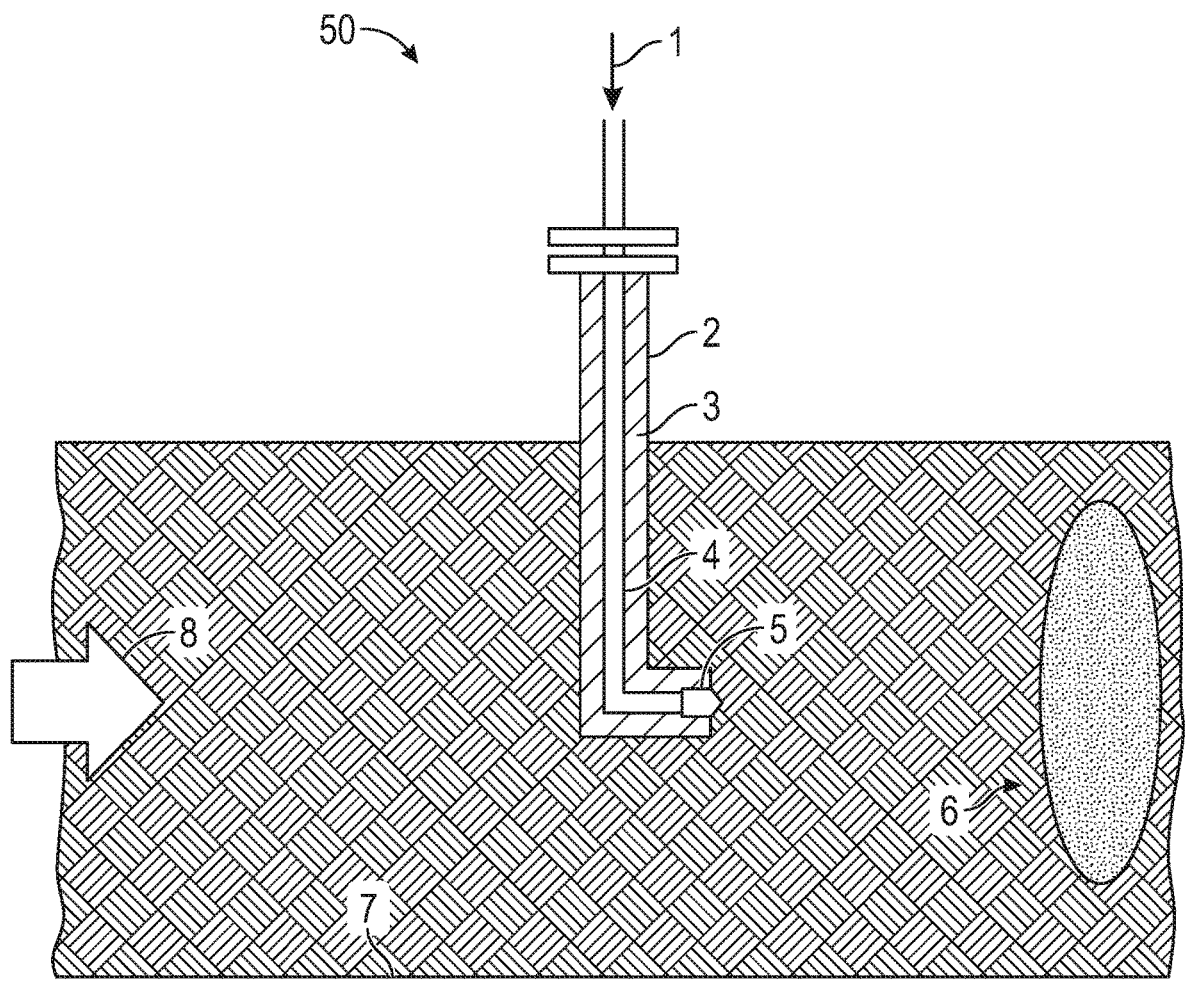
FIG. 2 is a simplified process flow diagram of a system for injecting a compound into a dehydrogenation process according to embodiments herein.
Figure 3:
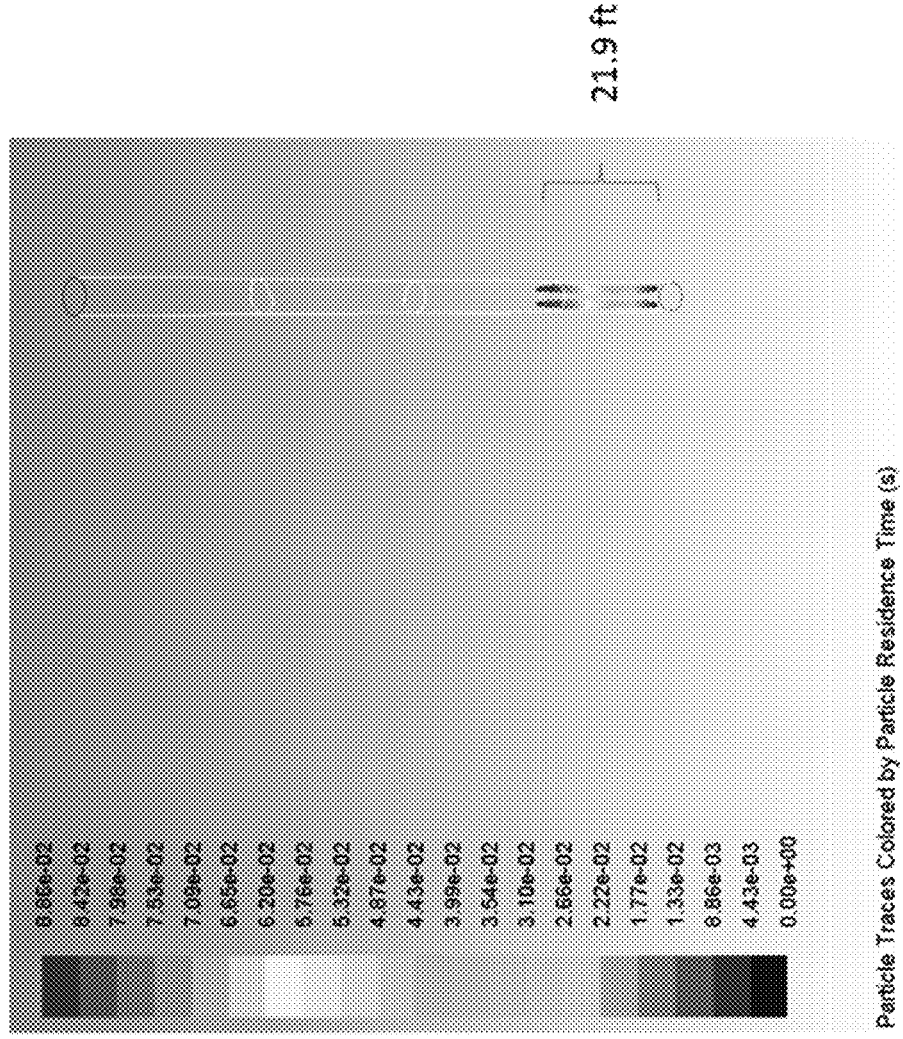
FIG. 3 presents graphical result of simulations injecting compounds into a flow stream of a dehydrogenation process according to embodiments herein.

A simplified flow diagram of a system 50 for injecting a potassium solution, without boiling the solution, is illustrated in FIG. 2. The main EB/steam feed 8 is traversing through pipe 7 toward reactor inlet 6. A potassium solution 1 is fed through an injection nozzle assembly, which may include a feed pipe 4, nozzle 5, and shell 2, and insulation 3. The insulation layer 3 surrounds and maintains a temperature of the potassium solution within feed pipe 4 at a temperature below its boiling point all the way up to nozzle 5, where the liquid solution is atomized into the EB/steam feed 8. Because the potassium solution is maintained as a liquid within pipe 4 all the way to nozzle 5, nozzle fouling may be minimized or eliminated.

The type of insulation and the thickness of the insulation layer needed to prevent boiling of the potassium solution will depend on the potassium salt or compound used, as well as the expected flow rate of the solution travelling through the pipe to the injection nozzle. Higher boiling solutions and higher flow rates of the solutions will require less insulation. The flow rate of the solution may be used to target injection of the potassium into the reactor feed at a concentration between 0.01 and 10 ppm by weight. In some embodiments, the solution feed line may be insulated. In other embodiments, the solution feed line may be cooled via heat exchange with water or other cool or cold heat exchange mediums, such as via heat exchange tracing, for example, where the heat exchange tracing may include annular piping or coils wrapped around the solution feed pipe. The annular piping or coils may encompass the solution feed line at least proximate the EB, steam, or EB/steam injection location, such as at least within a few feet, to negate any heat exchange with the significantly hotter EB, steam, or EB/steam piping and feed.

As described above, the system as illustrated in FIG. 2 may be used to continuously or intermittently inject a potassium solution into the feed stream. A pipe 4 including a jacket 2 may also be used, where a heat exchange medium 3 is circulated through the pipes to maintain the potassium solution as a liquid up to the injection nozzle 5. One skilled in the art, based on the above discussions, can also envision a jacket 2 being used to provide a heating medium 3 in the annular region, such as steam tracing, to maintain potassium metal as molten up to injection nozzle 5. Intermittent injection may include a continuous water flush, thereby maintaining movement of a solution or fluid through pipe 4.

For both molten potassium injection and potassium solution injection, it is also important to ensure that the solution or potassium vaporizes and mixes with the reactor feed. Accordingly, the spray angle of the nozzle can be configured to provide good distribution, as well as to atomize the injected metal or solution with an appropriate particle size to mix and vaporize without accumulating on the wall of the EB/steam feed pipe.

In some embodiments, there may be a single central spray nozzle 5 disposed in the center of the EB/steam feed pipe. In other embodiments, multiple injection nozzles may be located around the circumference of the pipe, spraying toward the center of the feed line; this could be a good way of distributing the potassium in cases where the feed pipe diameter is very large (several inches). In both embodiments, however, the spray nozzles should be oriented so that the salt solution or molten metal is kept away from the wall of the pipe, as much as practical, in order to minimize deposits and corrosion.

In some embodiments, it has been found advantageous to use fairly dilute solutions of potassium salt or potassium hydroxide. For example, 0.02 to 0.5 wt % solutions may be used. While seeming counter-intuitive, as the boiling point of the solution may be lower than for a concentrated solution, it has been found that having a lower solution viscosity will help the solution spray into smaller droplets and disperse/vaporize more readily. Having a low solution concentration also means that pure or essentially pure water may be continuously fed through the injector to keep it clear and clean. The potassium salt or potassium hydroxide could also be introduced intermittently, in some embodiments, to maintain catalyst activity. If the solution is fairly dilute, this would hardly impact process conditions. Further, a dilute solution may require a higher flow rate to introduce the same amount of potassium, and thus the insulation requirements to maintain the potassium solution below its boiling point may be decreased.

As described above, embodiments herein are directed toward a process for dehydrogenating an alkylbenzene, such as ethylbenzene, while maintaining catalyst activity. The process may include mixing a steam stream and an ethylbenzene stream to form an alkylbenzene/steam feed mixture. The alkylbenzene/steam feed mixture may then be fed to a dehydrogenation reactor, containing an alkali metal promoted catalyst, to dehydrogenate a portion of the alkylbenzene, such as the dehydrogenation of ethylbenzene to form styrene.

To maintain an activity of the alkali metal promoted catalyst, processes according to embodiments herein include injecting a liquid, selected from an alkali metal liquid, an alkali metal compound liquid, or a liquid solution comprising an alkali metal, into a feed stream comprising at least one of a steam stream, an alkylbenzene feed stream, or an alkylbenzene/steam feed mixture. The liquid is injected into the feed stream as a liquid, and the liquid vaporizes and disperses into the feed stream upstream of the dehydrogenation reactor.

In some embodiments, the alkali metal promoted catalyst comprises a potassium promoted catalyst. The alkali metal promoted catalyst may include an iron-based dehydrogenation catalyst in some embodiments. Numerous examples of suitable iron-based catalysts are described in U.S. Pat. No. 5,739,071, such as various catalysts including $Fe_2O_3$ promoted with potassium, for example. Other catalyst systems may also benefit from the injection methods disclosed herein, such as the injection of vanadium or vanadium compounds into a maleic anhydride reactor, for example.

In some embodiments, the alkali metal is injected as a liquid solution. The liquid solution may be, for example, a very dilute solution of an alkali metal compound or alkali metal salt in water. For example, a liquid solution containing an alkali metal may be an aqueous solution including 0.01 to 1.0 wt %, such as 0.02 to 0.5 wt % alkali metal in water.

Injection systems herein may be configured to maintain the liquid (i.e., the alkali metal, the alkali metal compound liquid, or the liquid solution comprising an alkali metal) in a liquid state from a point upstream of injection to the injection nozzle. The injection system may then be used to disperse the liquid through the injection nozzle and to form droplets of liquid dispersed in the feed stream, at which point the liquid injected may dissolve or evaporate into the vaporous feed stream.

In various embodiments, the injection nozzle may be configured to disperse droplets of the liquid, where the droplets may have an initial particle size of 100 microns or less, 75 microns or less, or 50 microns or less. As may be appreciated, the particle size of the droplets may decrease as the liquid is dispersed and dissolves into the vapor or otherwise evaporates. Accordingly, "initial" particle size relates to the size of the droplet particles as they are ejected from the injection nozzle.

In some embodiments, the injection nozzle may be disposed centrally within the feed stream (such as proximate a longitudinal axis of the feed stream pipe). In other embodiments, the liquid may be dispersed through two or more injection nozzles located circumferentially around the feed stream, where the nozzles are configured to spray co-current with the feed (such as EB, steam, or EB/steam) and toward a center of the feed stream. Co-current injection allows the liquids to be pulled downstream with the significantly larger steam/hydrocarbon mixture being fed to the reactor. Further, the co-current injection may be configured to avoid direct spray of the liquid onto the piping walls, thus minimizes accumulation of liquid droplets on the transfer piping.

Maintenance or restoration of catalyst activity may require continuous injection of an alkali metal or alkali metal compound in some embodiments. In other embodiments, the maintenance or restoration of catalyst activity may require only intermittent injection of the alkali metal or alkali metal compound. In some embodiments, for example, processes herein may include alternating injection of the liquid and injection of a pure water stream through the injection nozzle. In other words, the process may include intermittently stopping injection of the liquid and instead injecting pure water through the injection nozzle. The injection of water may be performed in a similar manner, where the water is maintained as a liquid up to the injection nozzle distributing the water. The intermittent presence of a pure water liquid stream may help maintain the walls of the piping and the injection nozzle clean, removing any accumulation of alkali metal or alkali metal compound that may have occurred due to normal operation or upsets.

In some embodiments, the process of injecting the liquid may include atomizing the liquid with an inert gas. For example, nitrogen, carbon dioxide, steam, argon, or other gases considered inert to the reaction system of interest may be used. The inert gas may be admixed with the liquid immediately upstream or within the distribution nozzle, enhancing the dispersion of the liquid into the steam/hydrocarbon transfer pipe at a desired initial particle size.

Following dispersion of the droplets into the steam or steam/hydrocarbon feed stream, the droplets may evaporate and disperse as a vapor into the feed stream. Full vaporization of the liquid upstream of the reactor entrance is desirable, so as to distribute the alkali metal or alkali metal compound throughout the catalyst beds, and avoiding settling of liquid on only the catalyst particles proximate the inlet. In some embodiments, for example, it has been found that the evaporating of the liquid may be accomplished within a distance of about 5 meters, 10 meters, or 15 meters, depending upon the atomization and initial particle size, stream temperatures, initial liquid droplet particle size, and other factors readily recognizable to one skilled in the art. Accordingly, the injection nozzle assembly and associated components may be located an appropriate distance upstream of the reactor inlet, such as at least 5 meters upstream of the reactor inlet, at least 10 meters upstream of the reactor inlet, or at least 15 meters upstream of the reactor inlet, in various embodiments. In some embodiments the injection nozzle is located in a main ethylbenzene/steam feed stream at a distance between about 5 meters and 10 meters upstream of the dehydrogenation reactor inlet.

In other embodiments, such as where the liquid may be injected into a main steam line 40, for example, it is preferred to have the liquid vaporize and disperse into the stream well in advance of any mixing, bends, or other portions of the piping system. Introducing the liquid too short of a distance in advance of such portions of the piping system may result in direct impingement of the atomized liquids, resulting in unwanted accumulation, restricted flow, and/or plugging of the piping components. Accordingly, the injection nozzle assembly and associated components may be located in a straight run of pipe an appropriate distance upstream of a bend, tee, or other piping components, such as at least 5 meters upstream of the piping components, at least 10 meters upstream of the piping components, or at least 15 meters upstream of the piping components, in various embodiments.

Embodiments herein are also directed toward a system for maintaining catalyst activity in a reactor. The system may include a liquid feed stream, such as a liquid alkali feed stream. The liquid alkali feed stream may be configured to maintain, in a liquid state, a liquid alkali feed selected from at least one of an alkali metal, an alkali metal compound liquid, and a liquid solution comprising an alkali metal. The system may also include an injection nozzle for injecting the liquid alkali feed, as a liquid, into a process feed stream selected from a steam stream, an alkyl aromatic (ethylbenzene) feed stream, and an alkyl aromatic (ethylbenzene)/steam feed stream, to form an alkali-containing feed upstream of a reactor. Systems herein may also include a dehydrogenation reactor containing an alkali metal promoted catalyst and having an inlet for receiving the alkali-containing feed or a mixture comprising the alkali-containing feed.

Systems according to embodiments herein may include an alkali feed stream that is steam traced, insulated, or coolant traced so as to maintain the alkali feed as a liquid upstream of the injection nozzle. In some embodiments, the injection nozzle may be disposed proximate an axial center of the process feed stream. In other embodiments, two or more injection nozzles may be disposed circumferentially about the process feed stream.

Systems herein may also include a water feed stream fluidly connected to the injection nozzle. Control systems and associated valving may also be used to intermittently inject a liquid water feed stream in lieu of the alkali feed stream. For example, the control system may be configured to alternate feed of the liquid alkali feed and the water feed stream to the injection nozzle.

EXAMPLE

Injection of a potassium hydroxide solution in water (1996 ppm KOH in water, by weight) was simulated. The solution was simulated as being injected into a pipe carrying the main steam feed to the reactor, where the solution was injected with a 75 micron droplet size. With a main steam line temperature simulated at 860° C., it was determined that the droplets would evaporate in about 21.9 feet of travel through the pipe. The simulated droplet size is illustrated in FIG. 2, where the particle traces are colored by particle residence times.

As described above, embodiments herein may provide for maintenance of catalyst activity by the injection of a liquid agent into a vaporous feed stream. Embodiments herein advantageously deliver the liquid agent, as a liquid, to the vaporous feed stream, thereby minimizing accumulation of salts or metals within and around the injection system and the associated piping.

While described above with respect to ethylbenzene dehydrogenation, injection systems disclosed herein may be used for other applications where a small quantity of non-volatile component needs to be injected into a gas phase. For example, systems herein may be used to inject small quantities of vanadium into the feed of a maleic anhydride reactor.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for dehydrogenating ethylbenzene, the process comprising:
    mixing a steam stream and an ethylbenzene stream to form an ethylbenzene/steam feed mixture;
    feeding the ethylbenzene/steam feed mixture to a dehydrogenation reactor containing an alkali metal promoted catalyst to convert a portion of the ethylbenzene to styrene;
    injecting a liquid comprising 0.02 to 0.5 wt % potassium hydroxide in water into a feed stream comprising at least one of the steam stream, the ethylbenzene stream, or the ethylbenzene/steam feed mixture, wherein the liquid evaporates and disperses into the feed stream upstream of the dehydrogenation reactor.

2. The process of claim 1, wherein the alkali metal promoted catalyst comprises a potassium promoted catalyst.

3. The process of claim 1, wherein the injecting comprises:
    maintaining the liquid in a liquid state from a point upstream of injection to an injection nozzle;
    dispersing the liquid through the injection nozzle to form droplets of liquid dispersed in the feed stream; and
    evaporating the liquid into the feed stream.

4. The process of claim 3, wherein the dispersed droplets have an initial particle size of 75 microns or less.

5. The process of claim 3, wherein the injection nozzle is disposed centrally within the feed stream.

6. The process of claim 3, comprising dispersing the liquid through two or more injection nozzles located circumferentially around the feed stream and configured to spray co-current with the feed and toward a center of the feed stream.

7. The process of claim 3, further comprising alternating injection of the liquid and injection of a pure water stream through the injection nozzle.

8. The process of claim 3, wherein the injecting comprises atomizing the liquid with an inert gas.

9. The process of claim 3, wherein the evaporating comprises evaporating the dispersed droplets into the feed stream within a distance of about 10 meters.

* * * * *